US010022501B2

(12) United States Patent
Olson (10) Patent No.: US 10,022,501 B2
(45) Date of Patent: Jul. 17, 2018

(54) MEDICAMENT DELIVERY DEVICE

(71) Applicant: Carebay Europe Ltd, Sliema (MT)

(72) Inventor: Stephan Olson, Danderyd (SE)

(73) Assignee: Carebay Europe, Ltd., Sliema (MT)

( * ) Notice: Subject to any disclaimer, the term of this patent is extended or adjusted under 35 U.S.C. 154(b) by 173 days.

(21) Appl. No.: 15/028,430

(22) PCT Filed: Oct. 8, 2014

(86) PCT No.: PCT/EP2014/071513
§ 371 (c)(1),
(2) Date: Apr. 10, 2016

(87) PCT Pub. No.: WO2015/052221
PCT Pub. Date: Apr. 16, 2015

(65) Prior Publication Data
US 2016/0250417 A1    Sep. 1, 2016

(30) Foreign Application Priority Data
Oct. 10, 2013  (SE) ...................... 1351201

(51) Int. Cl.
*A61M 5/315* (2006.01)
*A61M 5/20* (2006.01)
(Continued)

(52) U.S. Cl.
CPC ...... *A61M 5/31515* (2013.01); *A61M 5/2033* (2013.01); *A61M 5/2066* (2013.01);
(Continued)

(58) Field of Classification Search
CPC ............ A61M 5/31515; A61M 11/007; A61M 5/2033; A61M 5/2066; A61M 5/2448;
(Continued)

(56) References Cited

U.S. PATENT DOCUMENTS 4,202,314 A    5/1980    Smirrnov et al.

FOREIGN PATENT DOCUMENTS

FR    2741810 A1    6/1997
GB    2447787 A    9/2008
(Continued)

OTHER PUBLICATIONS

FR 2741810, Dreystadt, dateof publication: Jun. 6, 1997.*
(Continued)

*Primary Examiner* — Manuel Mendez
(74) *Attorney, Agent, or Firm* — McDonnell Boehnen Hulbert & Berghoff LLP (57) ABSTRACT

A medicament delivery device includes a housing, a container holder in the housing, an axially movable plunger, and an energy accumulating member adapted for displacing the plunger. The container holder is configured to accommodate a medicament container that includes a first piston arranged inside an opposite end portion of the container and a second piston arranged inside an intermediate portion of the container. The plunger includes an outer plunger rod, an inner plunger rod at least partially inside the outer plunger rod, a biassing arrangement for actuating the inner plunger rod, and a locking arrangement that, in a first state, locks the biassing arrangement in an energy-storing position and, in a second state, releases the biassing arrangement from the energy-storing position to displace the inner plunger rod into the container holder.

20 Claims, 7 Drawing Sheets

(51) Int. Cl.
*A61M 5/24* (2006.01)
*A61M 5/31* (2006.01)
*A61M 11/00* (2006.01)

(52) U.S. Cl.
CPC ........ *A61M 5/2448* (2013.01); *A61M 5/3129* (2013.01); *A61M 5/3157* (2013.01); *A61M 5/31583* (2013.01); *A61M 5/31585* (2013.01); *A61M 5/31596* (2013.01); *A61M 11/007* (2014.02); *A61M 11/00* (2013.01); *A61M 2005/206* (2013.01); *A61M 2005/2013* (2013.01); *A61M 2005/2474* (2013.01); *A61M 2005/3131* (2013.01); *A61M 2205/581* (2013.01); *A61M 2205/582* (2013.01)

(58) Field of Classification Search
CPC .............. A61M 5/3129; A61M 5/3157; A61M 5/31583; A61M 5/31585; A61M 5/31596

USPC .......................... 604/208, 134, 135, 136, 137
See application file for complete search history.

(56) References Cited

FOREIGN PATENT DOCUMENTS

| WO | 2012/085208 A1 | 6/2012 |
| WO | 2012/173553 A1 | 12/2012 |
| WO | 2015/052224 A1 | 4/2015 |

OTHER PUBLICATIONS

GB 2447787, Stamp et al., date of publication: Sep. 24, 2008.*
EPO, Int'l Search Report in PCT/EP2014/071513, dated Dec. 23, 2014.

* cited by examiner

MEDICAMENT DELIVERY DEVICE

TECHNICAL FIELD

Embodiments disclosed herein relate to medicament delivery devices for the administering of medicaments, in particular medicament delivery devices providing an automatic mixing of two medicament components, such as a liquid and a powder, or two liquids.

BACKGROUND

The present invention relates to medicament delivery devices such as automatic injection devices for injecting liquid medicament with a needle in a patient and nebulisers for administering a medicament in the form of a mist to be inhaled into the lungs of a patient.

Auto-injectors, or pen-injectors have been on the market for many years. During recent years some medicaments have been developed to be injected by patients themselves. Therefore, depending on the intended use and type of medicament, there have also been developed injection devices having a varying degree of automatic functions to facilitate the injection of medicaments in a reliable and safe way for patients and even for trained personnel; e.g. physicians and nurses.

WO 2012/173553 discloses an injection device comprising a housing and a container holder arranged within the housing. The container holder is configured for accommodating a medicament container having a needle attached to one end thereof and a stopper sealingly and slidable arranged inside the medicament container at the other end thereof. A plunger rod is arranged with a proximal end thereof contactable with the stopper. A first and a second energy accumulating member is arranged in the interior of the housing of the injection device and adapted to accumulate and store energy. A plunger drive means is slidably arranged in relation to the plunger rod, is rotationally locked to the plunger rod, and is rotatable in relation to the housing. The plunger drive means is operationally associated with the first energy accumulating member. A container driver is arranged for being connectable to the container holder and is threadedly connected to the plunger rod. The container driver is operationally associated with the second energy accumulating member such that due to an output axial force from the second energy accumulating member, the container holder and the plunger rod are axially moveable in relation to the housing a predetermined distance towards the proximal end of the injection device from an initial locked position to a second position whereby a needle penetration is performed. The plunger drive means is locked from being rotated by the container driver. The plunger drive means is released such that due to an output torque from the first energy accumulating member the plunger drive means is allowed to be rotated and the plunger rod is urged towards the proximal end of the injection device whereby an injection is performed.

Some medicaments administered via medicament delivery devices comprise two medicament components, which require mixing before being administered via a relevant medicament delivery device such as an injection device or a nebuliser.

In the context of a piston rod drive system for a manually operable drug delivery device WO 2012/085208 discloses a piston rod drive system comprising a main body adapted for coupling with a reservoir. A user operable activation element is operatively coupled with the main body and configured to move axially and rotationally relative to the main body between a first position and a second position to transfer a solvent from a rear chamber of a cartridge to a front chamber thereof. A piston rod element is operatively coupled with the activation element and the main body and configured to move axially and non-rotationally relative to the main body in response to the activation element being moved between the first position and the second position. The piston rod drive system and the drug delivery device as such do not lend themselves to be automated.

There exists a need for a medicament delivery device, which provides for an automated mixing of two medicament components.

SUMMARY

It is an object to provide a medicament delivery device, which provides for an automated mixing of two medicament components held in a medicament container.

According to an aspect, this is achieved by a medicament delivery device comprising:
a housing having a longitudinal axis extending between, and along, a proximal end portion and a distal end portion of the housing,
a container holder arranged in the housing at the proximal end portion,
an axially movable plunger adapted to be displaced along the longitudinal axis into the container holder, and
an energy accumulating member arranged inside the housing. The energy accumulating member is adapted for displacing the plunger along the longitudinal axis towards the proximal end portion. The container holder is adapted to accommodate a medicament container adapted for attachment of a medicament delivery member at one end portion of the medicament container and comprises a first piston sealingly and slidably arranged inside an opposite end portion of the medicament container, and a second piston slidably arranged inside an intermediate portion of the medicament container. The plunger comprises an outer plunger rod, an inner plunger rod arranged at least partially inside the outer plunger rod, a biasing arrangement for actuating the inner plunger rod, and a locking arrangement. The locking arrangement, in a first state, is arranged to lock the biasing arrangement in an energy storing position, and in a second state, is arranged to release the biasing arrangement from the energy storing position to displace the inner plunger rod along the longitudinal axis in a direction towards the proximal end portion into the container holder.

Since the biasing arrangement is releasable from the energy storing position to displace the inner plunger rod along the longitudinal axis in a direction towards the proximal end portion into the container holder, an automatic mixing of two medicament components in a medicament container held in the container holder is achieved. As a result, the above mentioned object is achieved.

The medicament delivery devices may be for instance be an injection device for injecting medicament in fluid form, or a nebuliser for administering a medicament in the form of a mist to be inhaled into the lungs. The medicament is at least partially administered powered by the first energy accumulating member displacing the plunger. The medicament delivery member may comprise a needle as used in an injection device, or a nozzle as used in a nebuliser.

According to embodiments, the biasing arrangement may be arranged inside the outer plunger rod at the distal end portion. In this manner the biasing arrangement may be readily available for biasing the plunger rod into the container.

According to embodiments, the biasing arrangement may comprise a compression spring extending along the longitudinal axis, which compression spring in the energy storing position may be subjected to an axial compression.

According to embodiments, the locking arrangement may comprise a compression rod extending along the longitudinal axis. When the locking arrangement is in the first state the compression rod is engaged with the compression spring and with the housing at the distal end portion to achieve the axial compression. In this manner the compression spring may be held in its energy storing position.

According to embodiments, the biasing arrangement may comprise a mixing torsion spring, which mixing torsion spring in the energy storing position is subjected to torsional loading.

According to embodiments, the locking arrangement may comprise a locking member attached to one end of the mixing torsion spring. The mixing torsion spring at an opposite end may be fixed in relation to the housing. When the locking arrangement is in the first state the locking member may be fixed in relation to the housing to achieve the torsional loading. In this manner the mixing torsion spring may be held in its energy storing position.

According to embodiments, the inner plunger rod may be adapted to engage with the outer plunger rod when the inner plunger rod is positioned in an end position towards the proximal end portion. In this manner it may be ensured that the inner plunger rod remains in a position towards the proximal end portion when the entire plunger is to be displaced towards the distal end portion to administer a medicament from the medicament container in the container holder.

According to embodiments, the inner plunger rod may comprise at least one resilient projection adapted to engage with a recess in the outer plunger rod when the inner plunger rod is positioned in the end position towards the proximal end portion. In this manner the inner plunger rod may engage with the outer plunger rod.

According to embodiments, the outer plunger rod may be provided with a series of elevations and/or depressions, and wherein the resilient projection may be adapted to run in abutment along the series of elevations and/or depressions when the inner plunger rod is moved towards the end position towards the proximal end portion to produce an audible and/or tactile feedback to a user of the medicament delivery device. In this manner a user may be made aware when a medicament mixing has been completed in the medicament delivery device. Accordingly, when the audible or tactile feedback has ended, the user will know that the medicament is ready to be administered.

According to embodiments, the energy accumulating member may comprise a main torsion spring for transferring stored energy into a rotational movement for the displacing of the plunger along the longitudinal axis in a direction towards the proximal end portion. In this manner a sufficient force for administering a medicament may be provided within a comparatively small space.

According to embodiments, the medicament delivery device may comprise a fixed member arranged inside the housing, the fixed member being provided with a threaded inner surface. The outer plunger rod may comprise a threaded outer surface, the threaded inner surface of the fixed member engaging with the threaded outer surface of the outer plunger rod. A first end of the main torsion spring may be connected to the housing and a second end of the main torsion spring may be connected to the outer plunger rod and may be releasably engaged with the housing. In this manner the torque from the main torsion spring may be transferred to the plunger rod. Moreover, energy may be stored in the main torsion spring until the second end of the main torsion spring is released from engagement with the housing.

According to embodiments, the outer plunger rod may be engaged with the second end of the main torsion spring via a drive member, the outer plunger being slidably connected with the drive member for sliding movement of the outer plunger rod along the drive member and the longitudinal axis. In this manner the torque from the main torsion spring may be transferred via the drive member to the plunger rod. The outer plunger rod will slide along the longitudinal direction in the drive member while the drive member is rotated. The rotation of the outer plunger member will advance the plunger towards the proximal end portion as the threaded outer surface of the outer plunger rod engage with the threaded inner surface of the fixed member.

Further features of, and advantages will become apparent when studying the appended claims and the following detailed description.

BRIEF DESCRIPTION OF THE DRAWINGS

Various aspects of embodiments, including their particular features and advantages, will be readily understood from the example embodiments discussed in the following detailed description and the accompanying drawings, in which.

DETAILED DESCRIPTION

Aspects of example embodiments will now be described more fully. Like numbers refer to like elements throughout. Well-known functions or constructions will not necessarily be described in detail for brevity and/or clarity.

Figure 1:
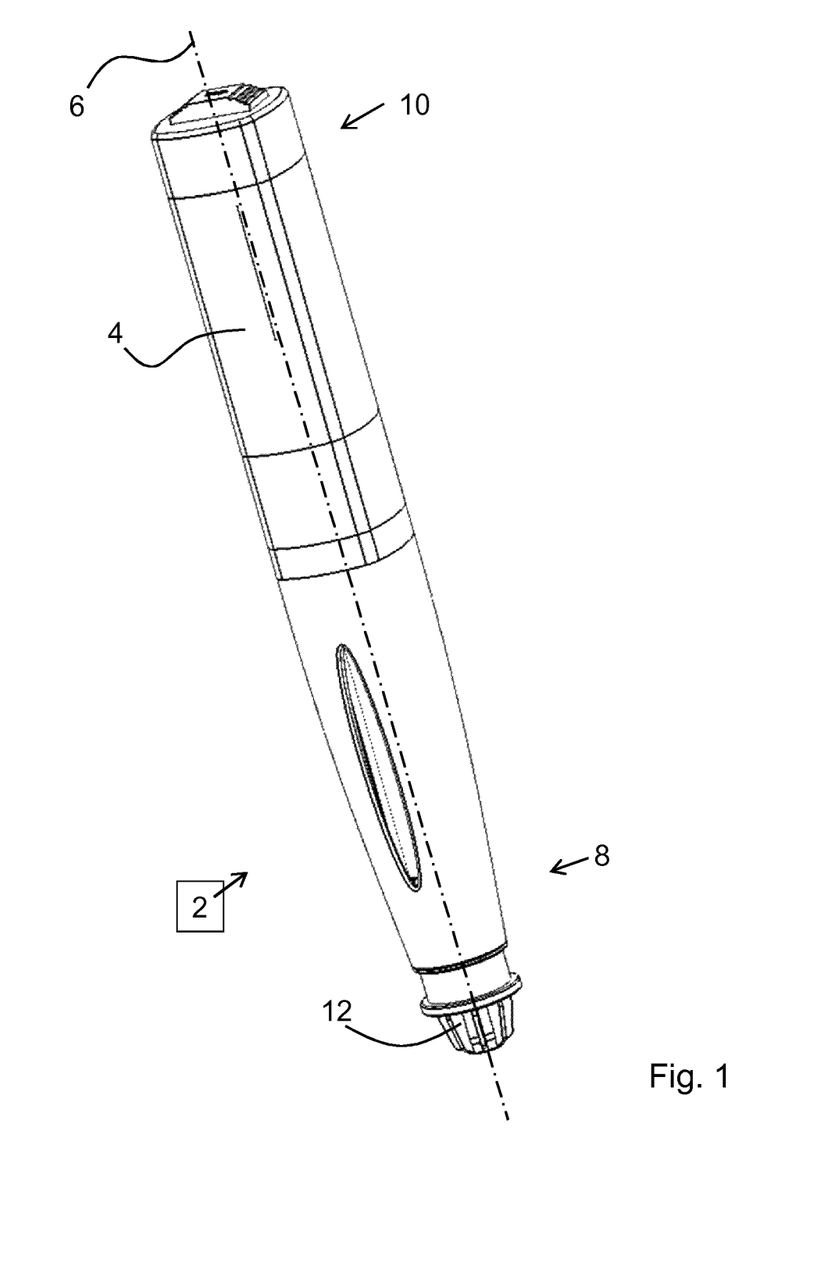
FIG. 1 illustrates a medicament delivery device according to embodiments.

FIG. 1 illustrates a medicament delivery device 2 according to embodiments. In these embodiments the medicament delivery device 2 is illustrated in the form of auto injector. The medicament delivery device 2 comprises a housing 4 having a longitudinal axis 6 extending between, and along, a proximal end portion 8 and a distal end portion 10 of the housing 4. A medicament delivery member in the form of a needle assembly is arranged at the proximal end portion 8. The needle assembly comprises a protective needle cover 12.

Figure 2:
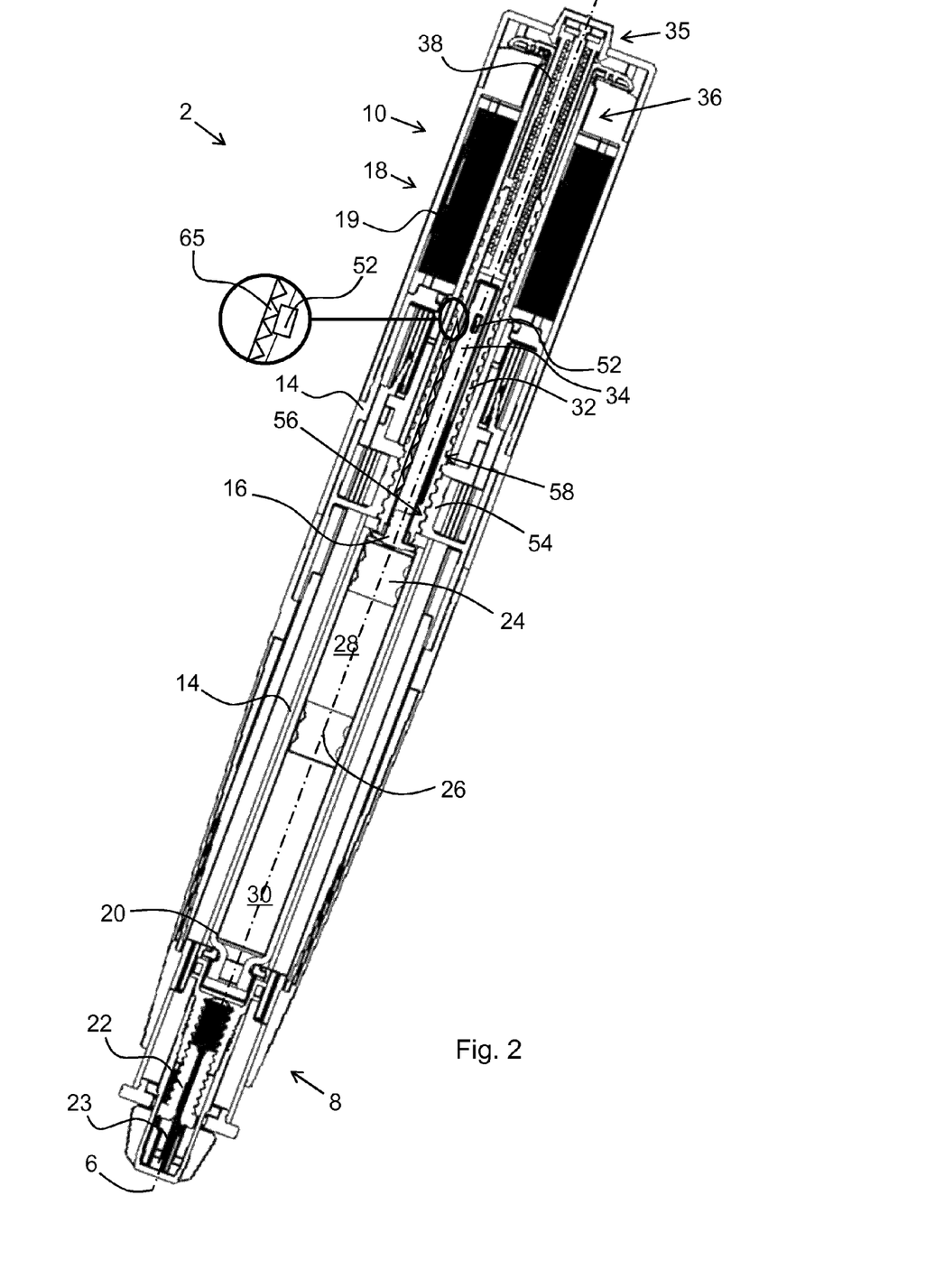
FIG. 2 illustrates a cross section through the medicament delivery device 2 illustrated in FIG. 1

FIG. 2 illustrates a cross section through the medicament delivery device 2 illustrated in FIG. 1. A container holder 14 is arranged in the housing 4 at the proximal end portion 8. An axially movable plunger 16 is adapted to be displaced along the longitudinal axis 6 into the container holder 14. An energy accumulating member 18 is arranged inside the housing 4.

The energy accumulating member 18 is adapted to displace the plunger 16 along the longitudinal axis 6 towards the proximal end portion 8. The energy accumulating member 18 comprises a main torsion spring 19 for transferring stored energy into a rotational movement for the displacing of the plunger 16 along the longitudinal axis in a direction towards the proximal end portion 8. The displacement of the plunger 16 will be discussed in more detail with reference to FIGS. 3 and 5 below.

The container holder 14 is adapted to accommodate a medicament container 20. The medicament container 20 is adapted for attachment of the medicament delivery member 22, comprising a needle 23 at a first end portion of the medicament container 20, at the proximal end portion 8 of the housing 4. The medicament container 20 comprises a first piston 24 sealingly and slidably arranged inside an opposite end portion of the medicament container 20, and a second piston 26 slidably arranged inside an intermediate portion of the medicament container 20.

Such a medicament container 20 is adapted to contain two medicament components, one of which is stored in a first space 28 between the first piston 24 and the second piston 26. The other medicament component is stored in a second space 30 between the first end portion of the medicament container 20 and the second piston 26. The two medicament components require mixing before being administered to a patient.

The plunger 16 comprises an outer plunger rod 32, an inner plunger rod 34 arranged at least partially inside the outer plunger rod 32, a biasing arrangement 36 for actuating the inner plunger rod 34, and a locking arrangement 35. The biasing arrangement 36 is arranged inside the outer plunger rod 32 at the distal end portion 10 of the housing 4. In these embodiments, the biasing arrangement 36 comprises a compression spring 38 extending along the longitudinal axis 6.

The locking arrangement 35, in a first state, is arranged to lock the biasing arrangement 36 in an energy storing position. In the energy storing position the compression spring 38 is subjected to an axial compression. In a second state, the locking arrangement 35 is arranged to release the biasing arrangement 36 from the energy storing position. When released, the biasing arrangement 36 will displace the inner plunger rod 34 along the longitudinal axis 6 in a direction towards the proximal end portion 8 into the container holder 14 and the medicament container 20.

Figure 3:
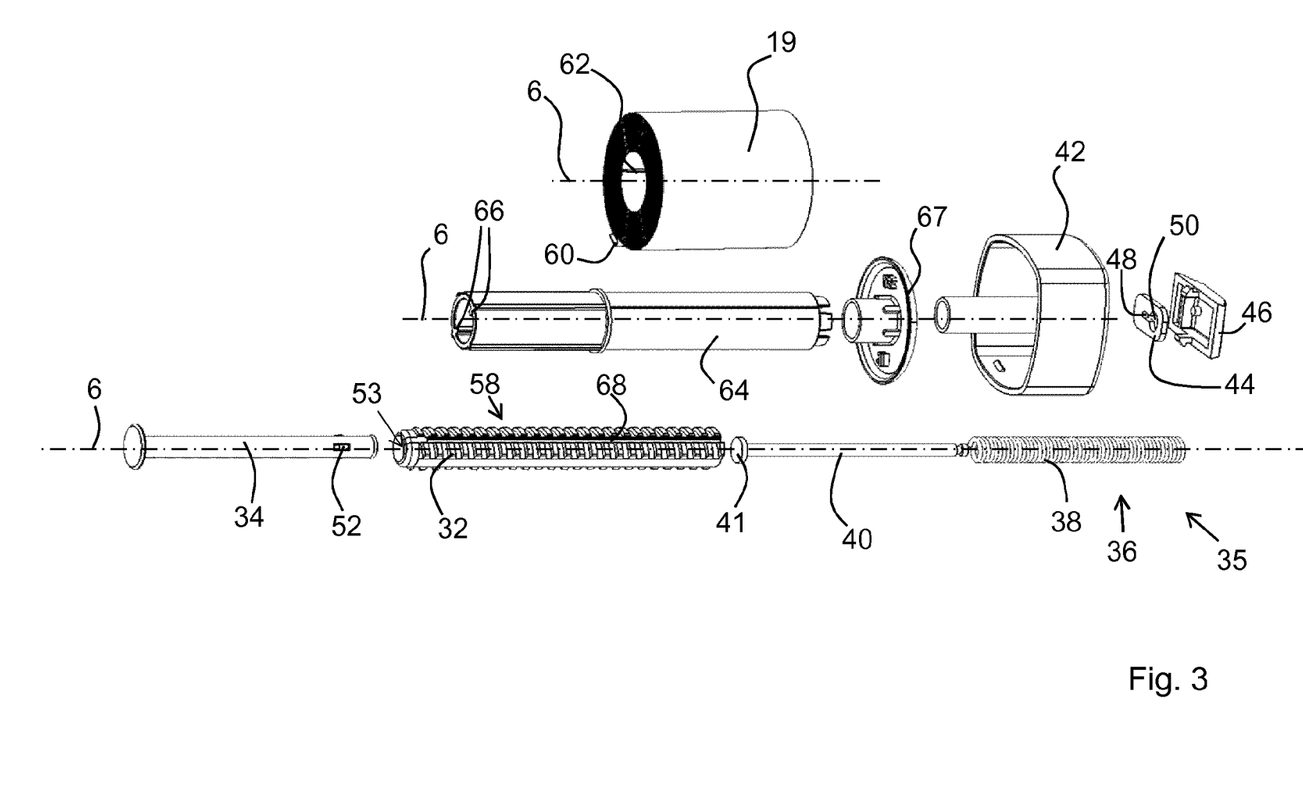
FIG. 3 illustrates a plunger, a biasing arrangement, a locking arrangement, and an energy accumulating member of a medicament delivery device according to embodiments.

FIG. 3 illustrates the plunger 16, the biasing arrangement 36, the locking arrangement 35, and the energy accumulating member 18 of the FIGS. 1 and 2 embodiments in an exploded view.

The compression spring 38 of the biasing arrangement 36 is a spiral spring. The locking arrangement 35 comprises a compression rod 40 extending along the longitudinal axis 6. The compression spring 38 extends about the compression rod 40, see FIG. 2. When the locking arrangement 35 is in the first state the compression rod 40 is engaged with the compression spring 38 and with the housing at the distal end portion to achieve the axial compression. Thus, the compression spring 38 is compressed between a wide portion 41 of the compression rod 40 and the housing. In FIG. 3 an end section 42 of the housing is shown. In an assembled state, the compression spring 38 extends partially through the end section 42 and the compression rod 40 extends through the end section 42. The locking arrangement 35 comprises a locking disc 44 arranged to engage with the compression rod 40. The locking disc 44 abuts slidably against the end section 42. In an assembled state, a button 46 engages with the locking disc 44. In the first state, the locking disc 44 engages with the compression rod 40. A narrow portion 48 of the compression rod 46 fits in a narrow aperture portion 48 of the locking disc 44. To shift the locking arrangement 35 into the second state, a user slides the button 46 and the locking disc 44 along the end section 42 such that a wide aperture portion 50 of the locking disc 44 is aligned with the compression rod 40 to release the compression rod 40.

Figure 4:
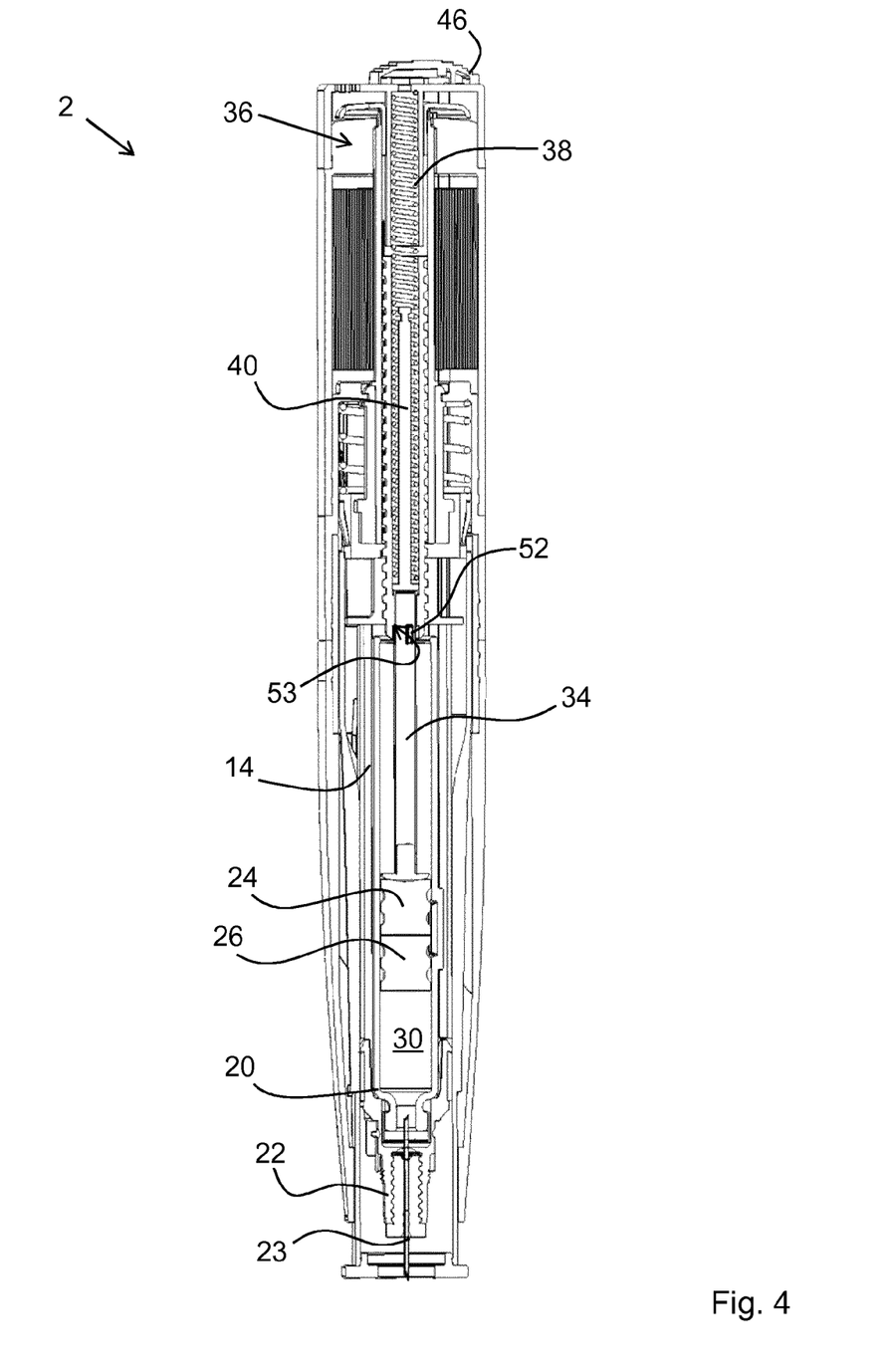
FIGS. 4-6 illustrate cross sections through the embodiments of the medicament delivery device of FIGS. 1-2.

The inner plunger rod 34 is adapted to engage with the outer plunger rod 32 when the inner plunger rod 34 is positioned in an end position towards the proximal end portion 8, see also FIG. 4. For this purpose, the inner plunger rod 34 comprises at least one resilient projection 52 adapted to engage with a recess 53 in the outer plunger rod 32 when the inner plunger rod 34 is positioned in the end position towards the proximal end portion.

In the following reference is made to FIGS. 3 and 2. A fixed member 54 is arranged inside the housing 4. The fixed member 54 is provided with a threaded inner surface 56. The outer plunger rod 32 comprises a threaded outer surface 58. The threaded inner surface 56 engages with the threaded outer surface 58.

A first end 60 of the main torsion spring 19 is connected to the housing 4 and a second end 62 of the main torsion spring 19 is connected to the outer plunger rod 32. The second end 62 is furthermore releasably engaged with the housing 4. In these embodiments the second end 62 is connected to the outer plunger rod 32 via a drive member 64. Accordingly, the outer plunger rod 32 engages with the second end 62 of the main torsion spring 19 via the drive member 64. The outer plunger 32 is slidably connected with the drive member 64 for sliding movement of the outer plunger rod 32 along the drive member 64 and the longitudinal axis 6. Such a slidable connection may for instance be achieved by an inner side of the drive member 64 being provided with at least one ridge 66 extending along the longitudinal axis 6 and an outer side of the outer plunger rod 32 being provided with at least one ridge recess 68 extending along the longitudinal axis 6. The at least one ridge 66 fits slidably in the at least one ridge recess 68.

Thus, when the second end 62 of the main torsion spring 19 is released, the stored energy from the main torsion spring 19 is transferred as a torque via the drive member 64 to the outer plunger rod 32. The drive member 64 and the outer plunger rod 32 will be rotated by the main torsion spring 19. While rotating, seen in a direction along the longitudinal axis 6, the drive member 64 remains stationary while the outer plunger rod 32, with its threaded outer surface 58 engaging with the threaded inner surface 56 of the fixed member 54, is moved towards the proximal end portion 8.

An injection indicator is provided in the form of a rotor 67 connected to the drive member 64. The end section 42 of the housing is provided with an opening (not shown). A face of the rotor 67 visible through the opening is coloured in at least two different colours. As the rotor 67 rotates with the drive member 64 the two different colours will be alternatingly visible in the opening as long as the drive member 64 is rotated by the main torsion spring 19. A user will thus be made aware that the injection is in progress. Similarly, the user will see that the injection is completed when the colours in the opening stop alternating.

Returning to FIG. 2, herein the medicament delivery device 2 is illustrated in an initial state with the biasing arrangement 36 in its energy storing position, the medicament container 20 with medicament components unmixed, and with the medicament container 20 not yet primed with the medicament delivery member 22.

The outer plunger rod 32, on its inside, is provided with a series of elevations and/or depressions 65. The at least one resilient projection 52 is adapted to run in abutment along the series of elevations and/or depressions 65 when the inner plunger rod 32 is moved towards the end position towards the proximal end portion 8 to produce an audible and/or tactile feedback to a user of the medicament delivery device 2.

FIG. 4 illustrates a cross section through the embodiments of the medicament delivery device 2 of FIGS. 1-3. In FIG. 4 the medicament delivery device 2 is illustrated in an intermediate state with the inner plunger rod 34 displaced by the biasing arrangement 36, the medicament container 20 with medicament components mixed in its second space 30, and with the medicament container 20 primed with the medicament delivery member 22.

Compared to the medicament delivery device 2 illustrated in FIG. 2, the button 46 has been slid along the housing 4 by a user to release the compression rod 40. The compression spring 38 has displaced the inner plunger rod 34 into the container holder 14 and the medicament container 20. Thus, the first piston 24 has been displaced towards the second piston 26. The at least one resilient projection 52 of the inner plunger rod 34 has engaged with the recess 53 of the outer plunger rod 32. Thereafter, the user has primed the medicament container 20 by moving the needle 23 of the medicament delivery device 22 into the medicament container 20. The medicament delivery device 2 is now ready for injecting the medicament into a patient.

Figure 5:
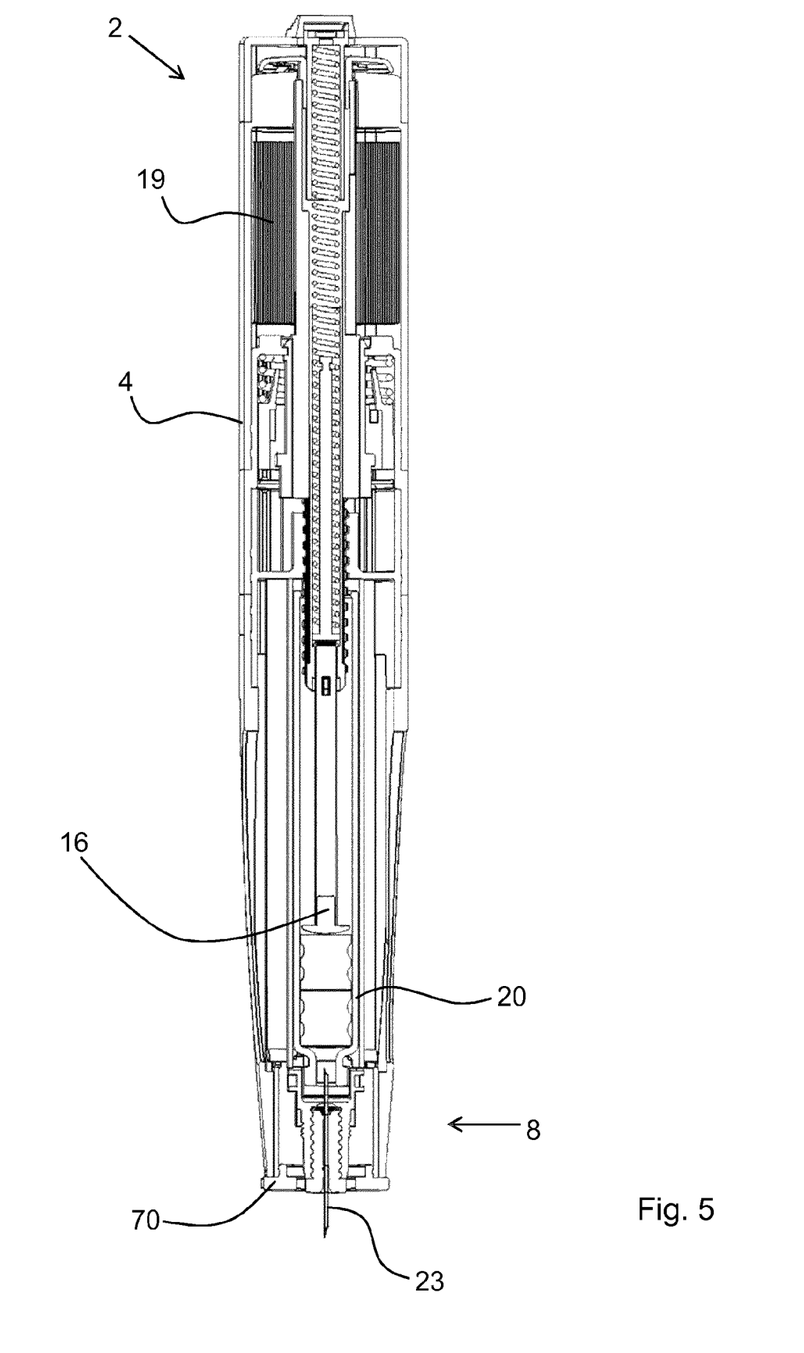

FIG. 5 illustrates a cross section through the embodiments of the medicament delivery device 2 of FIGS. 1-4. In FIG. 5 the medicament delivery device 2 is illustrated after injection of the medicament.

Compared to the medicament delivery device 2 illustrated in FIG. 4, the distal end portion 8 of the housing 4 has been pressed against a body of the patient to insert the needle 23 into the body, whereupon an elongated needle cover 70 has been pushed into the housing 4. The elongated needle cover 70 releases the second end 62 of the main torsion spring 19 from its engagement with the housing 4. Whereupon the plunger 16 has been displaced by the main torsion spring 19 further into the medicament container 20 injecting the medicament via the needle 23 into the patient.

Figure 6:
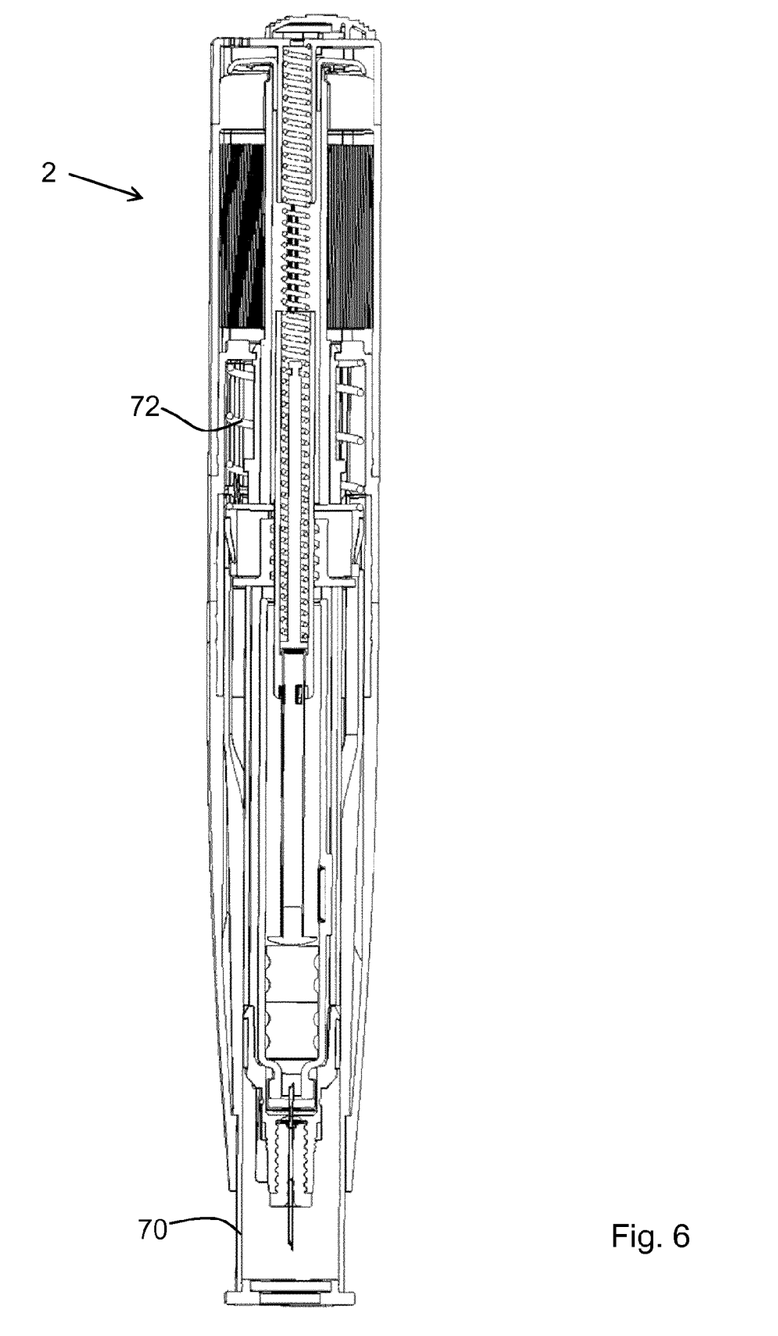

FIG. 6 illustrates a cross section through the embodiments of the medicament delivery device 2 of FIGS. 1-5. In FIG. 6 the medicament delivery device 2 is illustrated in a final needle protecting state.

Compared to the medicament delivery device 2 illustrated in FIG. 5, the medicament delivery device 2 has been removed from the body of the patient, whereupon the elongated needle cover 70 has been pushed to an outer position by an ejection spring 72. Thus the needle 23 is fully protected by the elongated needle cover 70. The elongated needle cover may be locked in the outer position.

Figure 7:
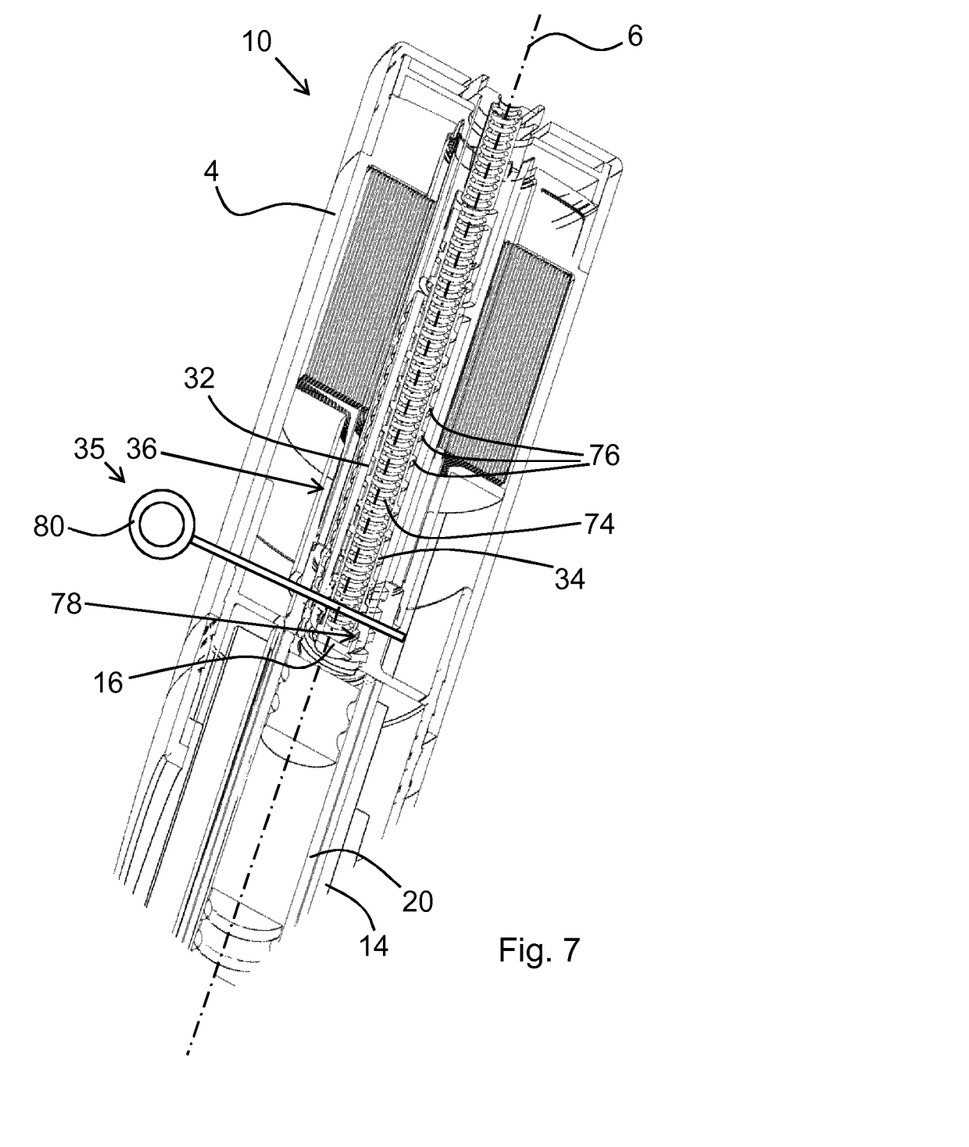
FIG. 7 illustrates a partial cross section through a medicament delivery device according to embodiments.

FIG. 7 illustrates a partial cross section through a medicament delivery device 2 according to embodiments. The medicament delivery device 2 according to these embodiments may in much correspondent to the embodiments illustrated in FIGS. 1-6. The main differences between these embodiments will be discussed below.

Again, a plunger 16 comprises an outer plunger rod 32, an inner plunger rod 34 arranged at least partially inside the outer plunger rod 32, a biasing arrangement 36 for actuating the inner plunger rod 34, and a locking arrangement 35. The biasing arrangement 36 is arranged inside the outer plunger rod 32 at a distal end portion 10 of a housing 4 of the medicament device 2. In these embodiments, the biasing arrangement 36 comprises a mixing torsion spring 74 extending along a longitudinal axis 6 of the housing 4.

The inner plunger rod 34 is provided with outer threads 76 and the outer plunger rod 32 is provided with inner threads 78. Thus, when rotated, the inner plunger rod 34 will be displaced at least partially out of the outer plunger rod 32.

The locking arrangement 35, in a first state, is arranged to lock the biasing arrangement 36 in an energy storing position. In the energy storing position, the mixing torsion spring 74 is subjected to torsional loading. In a second state, the locking arrangement 35 is arranged to release the biasing arrangement 36 from the energy storing position. When released, the biasing arrangement 36 will displace the inner plunger rod 34 along the longitudinal axis 6 in a direction towards a proximal end portion of the housing 4 into a container holder 14 of the housing 4 and a medicament container 20 arranged in the container holder 14, i.e. the mixing torsion spring 74 will rotate the inner plunger rod 34.

The locking arrangement 35 comprises a locking member 80 attached to one end of the mixing torsion spring 74. Moreover, the mixing torsion spring 74 is connected to the inner plunger rod 34. The locking member 80 may be connected to the mixing torsion spring 74 via the inner plunger rod 34. The mixing torsion spring 74 at an opposite end is fixed in relation to the housing 4. When the locking arrangement 35 is in the first state the locking member 80 is fixed in relation to the housing 4 to achieve the torsional loading. More specifically, in these embodiments the locking member 80 comprises a pin, which in the first state extends through the housing 4, and the outer and inner plunger rods 32, 34.

When the pin is removed, the mixing torsion spring 74 is released from its energy storing position. Thus, the inner plunge rod 34 is rotated by the mixing torsion spring 74.

This invention should not be construed as limited to the embodiments set forth herein. A person skilled in the art will realize that different features of the described embodiments may be combined to create embodiments other than those described herein, without departing from the scope of the present invention, as defined by the appended claims. It is also understood by those skilled in the art that the elongated needle cover 70 and the ejection spring 72 are optional features, which may be omitted in alternative embodiments. Again other embodiments may comprise an automatic needle penetration function. Embodiments implemented in a nebuliser, wherein the mixing of two medicament components is required before being administered, via a medicament delivery member comprising a nozzle, as a mist to be inhaled by a patient, are equally foreseen by the skilled person. Although the invention has been described with reference to example embodiments, many different alterations, modifications and the like will become apparent for those skilled in the art. Therefore, it is to be understood that the foregoing is illustrative of various example embodiments and that the invention is defined only the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A medicament delivery device, comprising:
   a housing having proximal and distal end portions, with a longitudinal axis extending between and along the proximal and distal end portions;
   a container holder arranged in the housing at the proximal end portion;
   an axially movable plunger adapted to be displaced along the longitudinal axis into the container holder; and an energy-accumulating member arranged inside the housing and adapted to displace the plunger along the longitudinal axis toward the proximal end portion;

wherein the container holder is adapted to accommodate a medicament container that is configured for attachment of a medicament delivery member at an end portion of the medicament container and that comprises a first piston sealingly and slidably arranged inside an opposite end portion of the medicament container and a second piston slidably arranged inside an intermediate portion of the medicament container; and the axially movable plunger comprises an outer plunger rod, an inner plunger rod arranged at least partially inside the outer plunger rod, a biassing arrangement for actuating the inner plunger rod, and a locking arrangement that, in a first state, is arranged to lock the biassing arrangement in an energy-storing position and, in a second state, is arranged to release the biassing arrangement from the energy-storing position to displace the inner plunger rod along the longitudinal axis toward the proximal end portion into the container holder, wherein the outer plunger rod is rotatable relative to the housing.

2. The medicament delivery device of claim 1, wherein the biassing arrangement is inside the outer plunger rod at the distal end portion.

3. The medicament delivery device of claim 1, wherein the inner plunger rod is adapted to engage the outer plunger rod when the inner plunger rod is positioned in an end position toward the proximal end portion.

4. The medicament delivery device of claim 3, wherein the inner plunger rod comprises at least one resilient projection adapted to engage a recess in the outer plunger rod when the inner plunger rod is positioned in the end position.

5. The medicament delivery device of claim 4, wherein the outer plunger rod includes a series of elevations and/or depressions, and the resilient projection is adapted to run in abutment along the series of elevations and/or depressions when the inner plunger rod is moved toward the end position, thereby producing an audible and/or tactile feedback to a user of the medicament delivery device.

6. The medicament delivery device of claim 1, wherein the biassing arrangement comprises a compression spring that extends along the longitudinal axis and, in the energy-storing position, is subjected to an axial compression.

7. The medicament delivery device of claim 6, wherein the locking arrangement comprises a compression rod that extends along the longitudinal axis, and when the locking arrangement is in the first state the compression rod engages the compression spring and the housing at the distal end portion, thereby generating the axial compression.

8. The medicament delivery device of claim 6, wherein the inner plunger rod is adapted to engage the outer plunger rod when the inner plunger rod is positioned in an end position toward the proximal end portion.

9. The medicament delivery device of claim 6, wherein the energy-accumulating member comprises a main torsion spring for transferring stored energy into rotational movement for displacing the plunger along the longitudinal axis toward the proximal end portion.

10. A medicament delivery device, comprising:
a housing having proximal and distal end portions, with a longitudinal axis extending between and along the proximal and distal end portions;
a container holder arranged in the housing at the proximal end portion;
an axially movable plunger adapted to be displaced along the longitudinal axis into the container holder; and
an energy-accumulating member arranged inside the housing and adapted to displace the plunger along the longitudinal axis toward the proximal end portion;
wherein the container holder is adapted to accommodate a medicament container that is configured for attachment of a medicament delivery member at an end portion of the medicament container and that comprises a first piston sealingly and slidably arranged inside an opposite end portion of the medicament container and a second piston slidably arranged inside an intermediate portion of the medicament container; and
the axially movable plunger comprises an outer plunger rod, an inner plunger rod arranged at least partially inside the outer plunger rod, a biassing arrangement for actuating the inner plunger rod, and a locking arrangement that, in a first state, is arranged to lock the biassing arrangement in an energy-storing position and, in a second state, is arranged to release the biassing arrangement from the energy-storing position to displace the inner plunger rod along the longitudinal axis toward the proximal end portion into the container holder,
wherein the energy-accumulating member comprises a main torsion spring for transferring stored energy into rotational movement for displacing the plunger along the longitudinal axis toward the proximal end portion.

11. The medicament delivery device of claim 10, further comprising a fixed member arranged inside the housing, the fixed member having a threaded inner surface; wherein the outer plunger rod comprises a threaded outer surface; the threaded inner surface of the fixed member is configured to engage the threaded outer surface of the outer plunger rod; a first end of the main torsion spring is connected to the housing; and a second end of the main torsion spring is connected to the outer plunger rod and releasably engages the housing.

12. The medicament delivery device of claim 11, wherein the outer plunger rod connects to the second end of the main torsion spring via a drive member, the outer plunger being slidably connected with the drive member for sliding movement of the outer plunger rod along the drive member and the longitudinal axis.

13. A medicament delivery device, comprising:
a housing having proximal and distal end portions, with a longitudinal axis extending between and along the proximal and distal end portions;
a container holder arranged in the housing at the proximal end portion;
an axially movable plunger adapted to be displaced along the longitudinal axis into the container holder; and
an energy-accumulating member arranged inside the housing and adapted to displace the plunger along the longitudinal axis toward the proximal end portion;
wherein the container holder is adapted to accommodate a medicament container that is configured for attachment of a medicament delivery member at an end portion of the medicament container and that comprises a first piston sealingly and slidably arranged inside an opposite end portion of the medicament container and a second piston slidably arranged inside an intermediate portion of the medicament container; and
the axially movable plunger comprises an outer plunger rod, an inner plunger rod arranged at least partially inside the outer plunger rod, a biassing arrangement for actuating the inner plunger rod, and a locking arrangement that, in a first state, is arranged to lock the biassing arrangement in an energy-storing position and, in a second state, is arranged to release the biasing arrangement from the energy-storing position to displace the inner plunger rod along the longitudinal axis toward the proximal end portion into the container holder, wherein the biasing arrangement comprises a mixing torsion spring that, in the energy-storing position, is subjected to a torsional load.

14. The medicament delivery device of claim 13, wherein the locking arrangement comprises a locking member attached to an end of the mixing torsion spring; the mixing torsion spring at an opposite end is fixed in relation to the housing; and when the locking arrangement is in the first state the locking member is fixed in relation to the housing, thereby generating the torsional load.

15. The medicament delivery device of claim 13, wherein the inner plunger rod is adapted to engage the outer plunger rod when the inner plunger rod is positioned in an end position toward the proximal end portion.

16. The medicament delivery device of claim 15, wherein the inner plunger rod comprises at least one resilient projection adapted to engage a recess in the outer plunger rod when the inner plunger rod is positioned in the end position.

17. The medicament delivery device of claim 16, wherein the outer plunger rod includes a series of elevations and/or depressions, and the resilient projection is adapted to run in abutment along the series of elevations and/or depressions when the inner plunger rod is moved toward the end position, thereby producing an audible and/or tactile feedback to a user of the medicament delivery device.

18. The medicament delivery device of claim 13, wherein the energy-accumulating member comprises a main torsion spring for transferring stored energy into rotational movement for displacing the plunger along the longitudinal axis toward the proximal end portion.

19. The medicament delivery device of claim 18, further comprising a fixed member arranged inside the housing, the fixed member having a threaded inner surface; wherein the outer plunger rod comprises a threaded outer surface; the threaded inner surface of the fixed member is configured to engage the threaded outer surface of the outer plunger rod; a first end of the main torsion spring is connected to the housing; and a second end of the main torsion spring is connected to the outer plunger rod and releasably engages the housing.

20. The medicament delivery device of claim 19, wherein the outer plunger rod connects to the second end of the main torsion spring via a drive member, the outer plunger being slidably connected with the drive member for sliding movement of the outer plunger rod along the drive member and the longitudinal axis.

* * * * *